United States Patent [19]
Cottrell et al.

[11] Patent Number: 5,281,538
[45] Date of Patent: Jan. 25, 1994

[54] METHOD OF PREPARING A SAMPLE FOR ANALYSIS BY LASER DESORPTION MASS SPECTROMETRY

[75] Inventors: John S. Cottrell, London, United Kingdom; Kuldip K. Mock, Sunnyvale, Calif.

[73] Assignee: Finnigan Mat Limited, United Kingdom

[21] Appl. No.: 835,971

[22] PCT Filed: Jun. 25, 1990

[86] PCT No.: PCT/GB90/00975

§ 371 Date: Feb. 20, 1992

§ 102(e) Date: Feb. 20, 1992

[87] PCT Pub. No.: WO91/04570

PCT Pub. Date: Apr. 4, 1991

[30] Foreign Application Priority Data

Sep. 12, 1989 [GB] United Kingdom ............... 8920639

[51] Int. Cl.$^5$ .................... G01N 24/00; G01N 1/00
[52] U.S. Cl. ..................... 436/173; 436/174; 436/178; 422/101; 250/281; 250/282; 250/423 R; 250/423 P
[58] Field of Search ............ 436/173, 174, 178; 422/101; 250/281, 282, 287, 423 R, 424, 423 P

[56] References Cited

U.S. PATENT DOCUMENTS 4,247,597 1/1981 Russell, Jr. .................... 428/403
5,045,694 9/1991 Beavis et al. .................... 250/282

FOREIGN PATENT DOCUMENTS 62-43562 2/1987 Japan ..................... G01N 27/62

OTHER PUBLICATIONS

Karas et al., "UV Laser Desorption/Ionization Mass Spect. of Femtomolar Amounts of Large Proteins", vol. 18, 1989, pp. 841–843.
Tanaka et al., "Detection of High Mass Molecules by Laser Desorption Time of Flight Mass Spect."
Karas et al., "UV Laser Matrix Desorption/Ionization . . . 100,000 Dalton Range", pp. 231–242.
Hillenkamp et al, "Matrix Assisted UV-Laser Desorption/Ionization", pp. 1–9.
Hillenkamp et al., "On Popping Corn, Erupting Volcanos, Tasting Wine, Massive Proteins and Related Matters", 1989, pp. 1–8.
Karas et al., "Laser Desorption/Ionization Mass Spect. of Proteins of Mass 100,000 to 250,000 Dalton", Ange. Chem. Jun. 1989 pp. 760–761.
Davis et al., "Identification of Naturally Occurring Quaternary Compounds by Combined Laser Desorption and Tandem Mass Spectrometry", Analytical Chemistry, vol. 55 No. 8 (Jul. 1983), pp. 1302–1305.
Karas et al., "Matrix Assisted Ultrviolet Laser Desorption of Non-volatile Compounds", International Journal of Mass Spectrometry and Ion Processes, vol. 78 (1987), pp. 53–68.
Shomo et al., "Laser Desorption Fourier Transform Ion Cyclotron Resonance Mass Spectrometry vs. Fast Atom Bombardment Magnetic Sector Mass Spectrometry for Drug Analysis", Analytical Chemistry, vol. 57 No. 14 (1985), pp. 2940–2944.
Wright et al., "Matrix Enhanced Laser Desorption in Mass Spectrometry and Tandem Mass Spectrometry", Biomedical Mass Spectrometry, vol. 12 No. 4 (1985), pp. 159–162.

Primary Examiner—James C. Housel
Assistant Examiner—Milton I. Cano
Attorney, Agent, or Firm—Flehr, Test, Hohbach, Albritton & Herbert

[57] ABSTRACT

A sample for analysis by Laser Desorption Mass Spectrometry is prepared by dissolving the sample material in a solvent and applying the solution to a matrix material applied to a target for a mass spectrometer. The matrix material is selected from the group consisting of (i) cis-Cinnamic Acid with the aromatic ring substituted by one or more groups which possess an electron pair on the atom adjacent to the ring; (ii) trans-Cinnamic Acid with the aromatic ring substituted by one or more groups which possess an electron pair on the atom adjacent to the ring; (iii) Benzoic Acid, with one or more substituent groups as described in (i); and (iv) Coumarin, with one or more substituent groups as described in (i).

4 Claims, No Drawings

METHOD OF PREPARING A SAMPLE FOR ANALYSIS BY LASER DESORPTION MASS SPECTROMETRY

This invention relates to a method of preparing a sample for analysis, and particularly a sample for analysis by Laser Desorption Mass Spectrometry (LDMS) in which ions are sputtered from a condensed phase sample surface by photon bombardment and are then subjected to mass analysis.

Many methods of LDMS are known, and a feature common to many is the use of a matrix material in which the analyte (the sample material to be analysed) is dispersed. The matrix material can serve one or more of a plurality of functions. For example it may act as a mediator in transferring energy from the photon bombardment to the sample material molecules; it may provide a physical and chemical environment which enhances the probability of desorption in the desired state of charge and aggregation; it may remove excess energy from the desorbed species through evaporation of matrix material molecules from a desorbed cluster of sample material and matrix material ions; and it may assist in the isolation and purification of the sample material.

Four techniques for using a matrix material to enhance LDMS have been described as set out below.

The first is to dissolve the sample material together with a 10:1 excess of an inorganic salt in a solvent, place a drop of the solution on the target surface, and evaporate to dryness as described by D. V. Davis et. al. in Analytical Chemistry, 55 1302 (1983). The sample material deposit is then irradiated with infra-red photons from a pulsed Neodymium YAG laser.

The second is to mix equimolar amounts of sample material and an inorganic salt in a droplet of glycerol placed on the target surface as described by L. G. Wright et. al. in Biomedical Mass Spectrometry, 12 159 (1985). The sample mixture is then irradiated with infra-red photons from a continuous wave carbon dioxide laser.

Thirdly, Japanese Patent Specification JP62-43562 discloses a sample preparation technique in which a solution of the sample material is mixed with a slurry of glycerol and fine cobalt powder. A droplet of the mixture is then irradiated with ultraviolet photons from a pulsed nitrogen laser.

Fourthly, M. Karas et. al. (Int. J. Mass Spectrom. Ion Processes, 78 53 (1987)) describe using a large molar excess of a matrix material which has a strong absorption at the wavelength of the incident radiation. For example, the sample material is dissolved in a solution containing a thousand-fold molar excess of Nicotinic Acid. A drop of the solution is placed on the target surface, evaporated to dryness, and irradiated with 266 nm ultraviolet photons from a frequency quadrupled pulsed Neodynium YAG laser. The use of a matrix material which has a strong absorption for the incident photons represents an important distinction between this approach and the first three described because it allows the use of low power densities which increases the probability of desorbing intact molecular ions.

The use of 266 nm photons and a Nicotinic Acid matrix material as described in M. Karas et. al. mentioned above has been shown to provide excellent sensitivity. A drawback of the technique is that suitable sources of 266 nm photons are complex and expensive. The commonly used sources are a Q switched, frequency quadrupled Neodymium YAG laser or an excimer pumped, frequency doubled dye laser.

According to this invention there is provided a method of preparing a sample for analysis by laser desorption mass spectrometry, comprising dissolving the sample material in a solvent and applying the solution to a matrix material applied to a target for a mass spectrometer, in which the matrix material is selected from the group consisting of (i) Cinnamic Acid, either cis or trans, with the aromatic ring substituted by one or more groups which possess an electron pair on the atom adjacent to the ring; (ii) Benzoic Acid, with one or more substituent groups as described in (i); (iii) Coumarin, with one or more substituent groups as described in (i).

The method of this invention gives the advantage that it enables the use of relatively long wavelength photons, in particular 337 nm light from a commonly available nitrogen laser, for the photon bombardment, rather than it being necessary to use lasers as mentioned above.

The matrix material can be one of:
2,4-Dimethoxycinnamic Acid
3,4-Dimethoxycinnamic Acid
3,4-Dihydroxycinnamic Acid
4-Hydroxy-3-methoxycinnamic Acid
3-Hydroxy-4-methoxycinnamic Acid
3,5-Dimethoxy-4-hydroxycinnamic Acid Otherwise the matrix material can be Anthranilic Acid or Scopoletin.

This invention will now be described by way of example.

A matrix material selected from the group specified is dissolved in an appropriate solvent system, generally water, at a concentration of (say) $5 \times 10^{-2}$ molar. A small aliquot of a solution of the sample in a compatible solvent system, for example a $10^{-5}$ molar solution of a peptide in 0.1% aqueous Trifluoroacetic Acid, is mixed with an aliquot of the matrix solution and applied to a target for a mass spectrometer. Alternatively, the two solutions may be mixed directly on the target surface. The mixed solution is evaporated to dryness and the prepared target introduced into the source region of the mass spectrometer for analysis by bombardment with 337 nm photons from a nitrogen laser.

We claim:

1. A method of preparing a sample for analysis by laser desorption mass spectrometry, comprising dissolving the sample material in a solvent and applying the solution to a matrix material applied to a target for a mass spectrometer, in which the matrix material is selected from the group consisting of (i) cis-Cinnamic Acid, with the aromatic ring substituted by one or more groups which possess an electron pair on the atom adjacent to the ring; (ii) trans-Cinnamic Acid, with the aromatic ring substituted by one or more groups which possess an electron pair on the atom adjacent to the ring; (iii) Benzoic Acid, with the aromatic ring substituted by one or more groups which possess an electron pair on the atom adjacent to the ring; and (iv) Coumarin, with the aromatic ring substituted by one or more groups which possess an electron pair on the atom adjacent to the ring.

2. A method as claimed in claim 1, wherein the matrix material is selected from a group consisting of:
2,4-Dimethoxycinnamic Acid;
3,4-Dimethoxycinnamic Acid;
3,4-Dihydroxycinnamic Acid;
4-Hydroxy-3-methoxycinnamic Acid;
3-Hydroxy-4-methoxycinnamic Acid; and
3,5-Dimethoxy-4-hydroxycinnamic Acid.

3. A method as claimed in claim 1, in which the matrix material is Anthranilic Acid.

4. A method as claimed in claim 1, in which the matrix material is Scopoletin.

* * * * *